United States Patent [19]

Horiguchi

[11] Patent Number: 5,456,700
[45] Date of Patent: Oct. 10, 1995

[54] THERAPEUTIC DEVICE UTILIZING INFRARED RADIATION AND ELECTROSTATIC FIELD

[76] Inventor: Noboru Horiguchi, 2969-1, Kawatsu-cho, Sakaide-shi, Kagawa-ken, Japan

[21] Appl. No.: 149,649

[22] Filed: Nov. 9, 1993

[30] Foreign Application Priority Data

Nov. 12, 1992 [JP] Japan .................................. 4-302479

[51] Int. Cl.$^6$ ........................................................ A61N 1/40
[52] U.S. Cl. .................................. 607/50; 607/88; 607/96
[58] Field of Search .................................. 607/50, 88–91, 607/96–100, 115

[56] References Cited

U.S. PATENT DOCUMENTS

| 5,038,780 | 8/1991 | Boetzkes ................................ 607/50 |
| 5,133,352 | 7/1992 | Lathrop et al. ....................... 607/50 |

FOREIGN PATENT DOCUMENTS

| 2613629 | 10/1988 | France . |
| 1514767 | 6/1969 | Germany . |
| 2535621 | 2/1977 | Germany . |
| 8000918 | 5/1980 | WIPO . |

*Primary Examiner*—Lee S. Cohen
*Assistant Examiner*—Robert L. Nasser, Jr.
*Attorney, Agent, or Firm*—Lorusso & Loud

[57] ABSTRACT

A curative device for promoting healing of a subject is disclosed which includes a housing having an open end, an infrared lamp secured within the housing and adapted to radiate infrared rays, an oxygen-containing gas source, a gas diffusing pipe disposed within the housing and having a first end connected to the oxygen-containing gas source and a second end located adjacent to the open end and oriented so that the oxygen-containing gas is emitted from the second end in the axial direction of the housing, a DC voltage source, and an electrode disposed adjacent to the second end of the gas diffusing pipe and electrically connected to the DC voltage source and adapted to form an electrostatic field in the atmosphere adjacent to the open end of the housing. When the housing is positioned such that the open end is oriented toward and spaced apart from the subject, the subject can be exposed to the electrostatic field and a flow of the oxygen-containing gas and irradiated with the infrared rays.

9 Claims, 7 Drawing Sheets

THERAPEUTIC DEVICE UTILIZING INFRARED RADIATION AND ELECTROSTATIC FIELD

BACKGROUND OF THE INVENTION

This invention relates to a therapeutic device useful for promoting the healing of a living organism and for the promotion of health thereof.

A variety of methods have been proposed for improving or strengthening the inherent, healing force of living organisms, especially human being, with or without resorting to medicines. When the body's own healing capacity is low, the affliction is not easily treated even with a repeated dosage of medicines. On the other hand, an affliction in a man having good healing capacity can be often remedied even without resorting to a medical treatment. Known methods for promoting healing include, for example, a method in which a heat is applied to a diseased part, a method in which a diseased part is exposed to a magnetic field and a method in which a subject is contacted with a static electrode. The conventional methods, however, are not fully satisfactory with respect to promotion of healing.

SUMMARY OF THE INVENTION

In accordance with the present invention there is provided a therapeutic device comprising:

an axially extending housing member having an open end;

an infrared lamp secured within said housing member so that infrared radiation from said lamp passes outwardly through said open end upon energization of said lamp;

means for feeding an oxygen-containing gas to the device;

a gas diffusing pipe disposed within said housing member and having a first end connected to said oxygen-containing gas feeding means and a second end located adjacent to said open end and oriented so that the oxygen-containing gas is diffused from said second end axially of said housing member upon actuation of said oxygen-containing gas feeding means;

means for applying a DC voltage; and an electrode disposed adjacent to said second end of said gas diffusing pipe and electrically connected to said DC voltage applying means so that an electrostatic field is formed in the atmosphere adjacent to said open end of said housing member upon actuation of said DC voltage applying means, whereby when said housing member is positioned such that said open end is oriented toward and spaced apart from an object, the object can be exposed to the electrostatic field and flow of the diffused oxygen-containing gas and to infrared radiation.

The healing quality improving effect obtained by the present invention is considered to be attained by the following mechanism.

When an oxygen-containing gas contacts an affected part of a subject, cutaneous respiration is accelerated. Oxygen is one of the most important elements constituting biopolymers. In addition, oxygen serves as an energy source for living tissues and cells. Generally, oxygen is introduced into blood through pulmonary respiration and is fed to cells to produce ATP (adenosine triphosphate) by the mitochondria. ATP serves as an energy source for cells and promotes metabolism thereof. Intake of oxygen into cells is also effected by cutaneous respiration. An average human being has about 1.5 $m^2$ of the skin surface area. Therefore, acceleration of the cutaneous respiration promotes metabolism of the cells. Additionally, a flow of the oxygen-containing gas against the skin of the subject creates an electric field which serves to act on ions in the blood and to accelerate physiological functions.

The infrared ray radiation is effective as thermotherapy. The kinetic energy of molecules constituting tissues is increased upon absorption of IR so that the temperature of the tissues is increased and the peripheral capillary vessels are expanded. Thus, the blood flow is accelerated so that the feed of nutrients and oxygen to the tissue cells and discharge of waste matters therefrom are accelerated. The waste matters including pain-causing substances are then eliminated from the subject through kidney-urinary passages.

Even though the tissue cells are activated and the metabolism is promoted by the IR irradiation combined with the contact with the oxygen-containing gas, the normal cellular functions cannot be maintained unless the environment to which the cells are exposed is suited for the growth thereof. Location of the diseased part of the subject in an electrostatic field is effective to improve the environment under which the cells of the diseased part grow. Namely, when the cells are placed in an electrostatic field, the concentration of $N^+$ ions outside of the cells is increased and that in the inside thereof is decreased, while the concentration of $K^+$ ions inside of the cells is increased and that outside thereof is decreased. As a result, the pH of the electrolyte liquid outside of the cells is increased to a value (pH: 7.4) suited for the growth of the cells.

More particularly, areas both inside and outside of the cells of living organisms are filled with an electrolyte liquid which is normally maintained at 7.4 by homeostasis. Once such an environment is destroyed and the pH is lowered to an acidic region, it is not easy for the living organism to restore its normal environment. Upon being subjected to an electrostatic field having a suitable field intensity, the electrolytes outside of the cells are made favorable to $Na^+$, $Cl^-$, $Ca^{++}$ and $HCO_3^-$ while the electrolytes inside of the cells are made favorable to $K^+$ and $Mg^{++}$, so that the pH of the electrolyte liquid is increased toward the suitable value. Maintenance of the pH at 7.4 is also desirable for obtaining effective utilization of ATP.

It is, therefore, an object of the present invention to provide a therapeutic device for increasing and strengthening the healing force within living organisms, especially animals inclusive of human beings.

Another object of the present invention is to provide a therapeutic device which is effective to cure diseased or affected parts of living organisms.

It is a further object of the present invention to provide a therapeutic device effective to treat various diseases such as neural dermatitis, dermatophytosis, mycotic dermatitis, "viral dermatitis, allergic dermatitis, stiffness in the shoulders, lumbago, myalgia, myotonic headache and insomnia."

BRIEF DESCRIPTION OF THE DRAWINGS

Other objects, features and advantages of the present invention will become apparent from the detailed description of the invention which follows, when considered in light of the accompanying drawings, in which.

DETAILED DESCRIPTION OF THE PREFERRED EMBODIMENTS OF THE INVENTION

Figure 1:
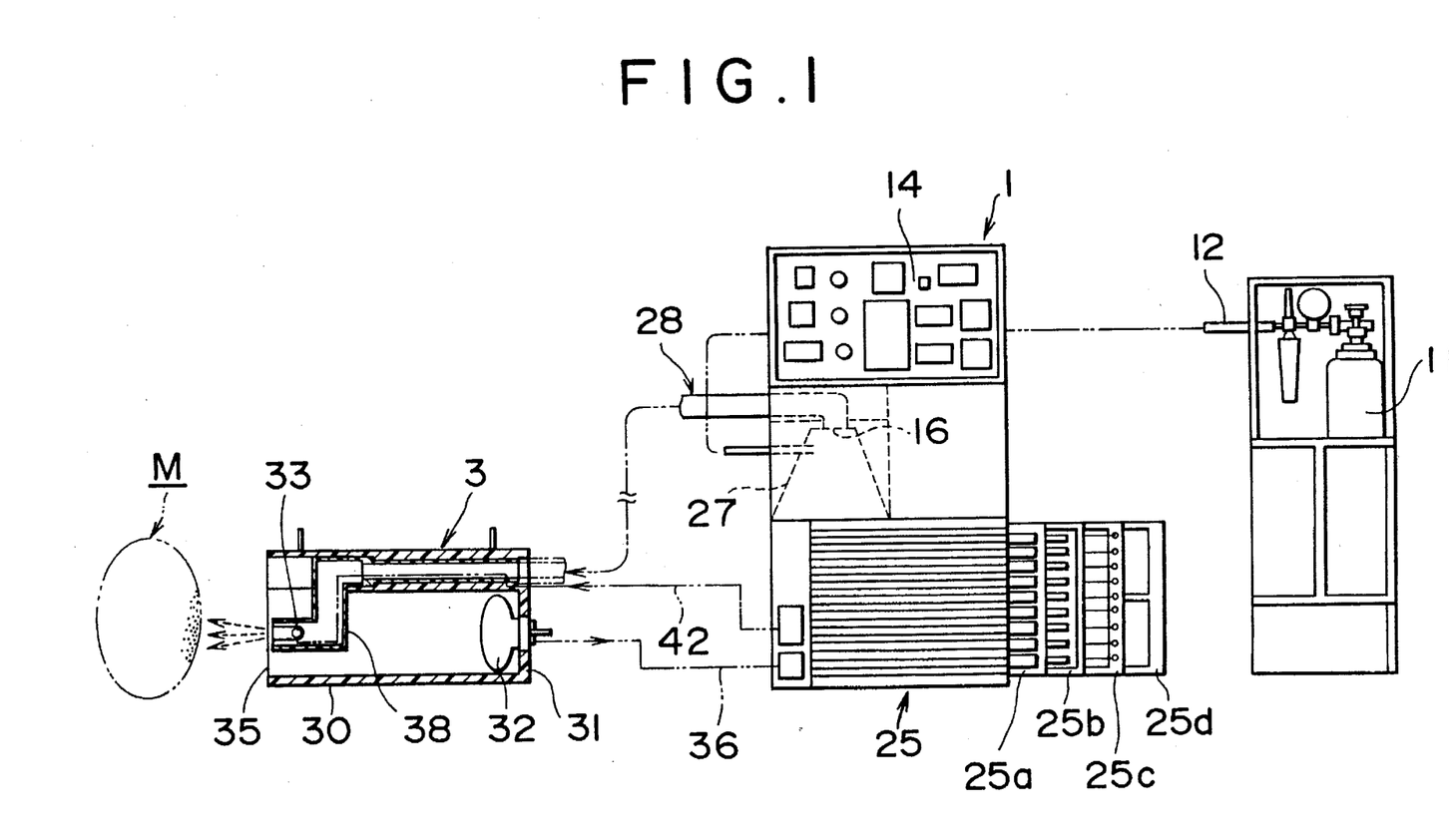
FIG. 1 is an elevational view, partly in cross-section, diagrammatically showing one embodiment of a curative device according to the present invention including an operation unit, and a controlling unit.

Referring to FIG. 1, a curative device according to the present invention includes a controlling unit 1 and an operation unit 3, preferably displaceable and positionable at any desired location relative to the controlling unit 1.

Figure 3:
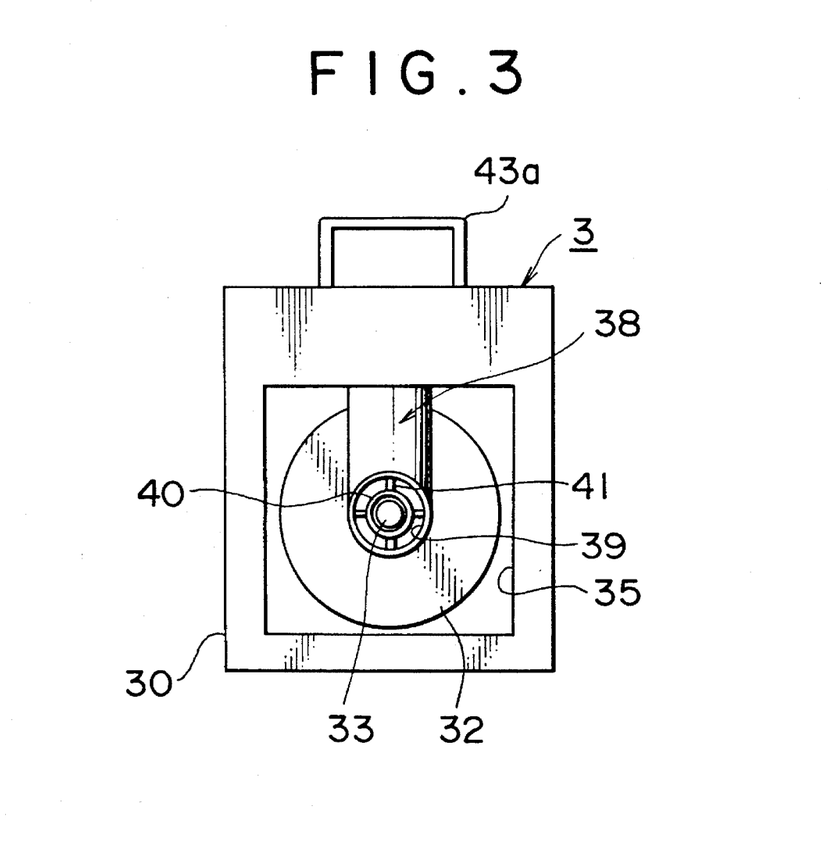
FIG. 3 is an enlarged, front view of the operation unit of FIG. 1.

The operation unit 3 includes an axially extending, generally tubular housing member 30, preferably formed of an electrically insulating material and open ended at its front end 35. As shown in FIG. 3, the housing member 30 in the illustrated embodiment has a rectangular cross section. If desired, however, the housing member 30 may be any other shape such as a cylindrical or cubic form.

Figure 2:
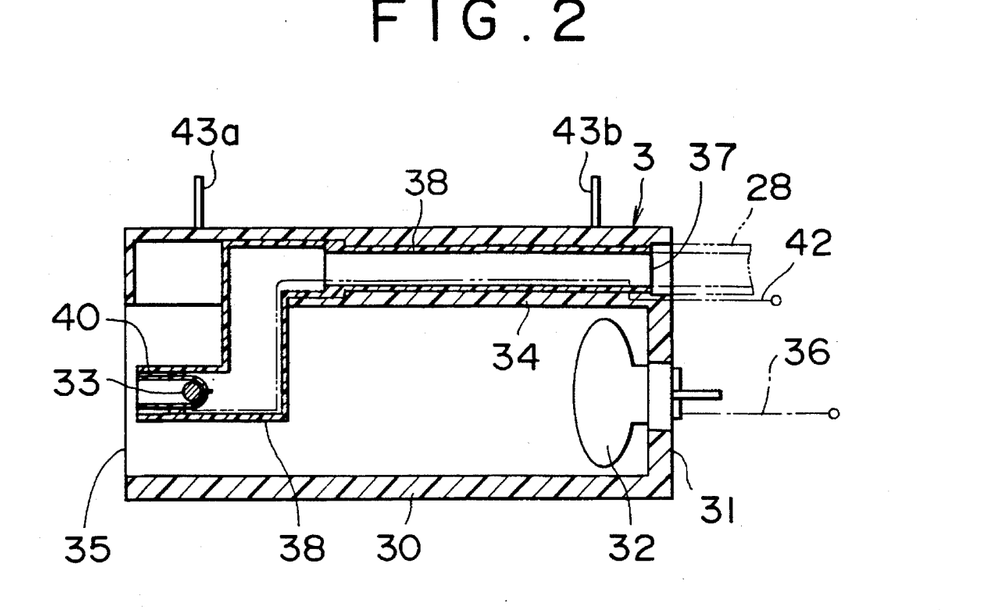
FIG. 2 is an enlarged, cross-sectional view of the operation unit of FIG. 1.

The housing member 30 has a rear, bottom plate 31 to which an infrared lamp 32 is fixed. The lamp 32 is electrically connected to an infrared lamp power source provided in the controlling unit 1 through an electric wire 36 so that infrared radiation from the lamp 32 passes outwardly through the front opening 35 upon energization of the lamp 32. By controlling the voltage impressed to the lamp 32, the intensity of the infrared radiation can be easily controlled. Generally, the intensity of the infrared radiation is controlled so that the thermotherapy by the infrared irradiation is performed at a temperature lower by 6°–14° C. than the body temperature of the subject to be treated.

A gas diffusing pipe 38 in a crank form and preferably formed of an electrically insulating material is disposed within said housing member 30. As shown in FIG. 2, the pipe 38 has a first open end 37 located at an upper portion of the rear plate 31 of the housing member 30 and extends in the axial direction thereof to a position nearer to the open end 35 of the housing member 30 than the closed end 31. The pipe 38 is then bent inwardly and again bent so that the end portion of the pipe 38 is oriented in parallel with the axis of the tubular housing member 30 and is located near the center of the opening 35 of the housing member 30. The second, open end 39 of the pipe 38 is generally positioned adjacent to and slightly inward from the opening 35 of the housing member 30. Designated as 34 is a support plate preferably formed of an electrically insulating material for fixedly securing the pipe 38 in position.

Coaxially disposed inside of the gas feeding pipe 38 at a position adjacent to the second end 39 is a cylindrical cover 40 preferably formed of an electrically insulating material and having a U-shaped, longitudinal cross section, so that an annular space is defined between the pipe 38 and the cover 40. The first end 37 of the pipe 38 is connected to an oxygen-containing gas feed port 16 provided in the controlling unit 1 through a pipe 28, preferably a flexible plastic pipe, so that an oxygen-containing gas may be diffused or injected outwardly from the second end 39, through the annular space, in the axial direction of the housing member 30. Designated as 41 is a holder for fixedly securing the cylindrical cover 40 to the pipe An electrode 33, preferably in a spherical shape having a diameter of 0.5–5 cm, is disposed inside of the cylindrical cover 40 at a position adjacent to the closed end thereof and is electrically connected to a high DC voltage source through a lead wire 42 so that an electrostatic field is formed in the atmosphere adjacent to the open end of the housing member upon energization of the electrode 33. The DC source has preferably such a voltage that the electrostatic field has a field intensity of 20–100 volts per meter. Generally a DC voltage of –1,000 to –7,000 volts is impressed to the electrode 33. Designated as 43a and 43b are a pair of handles to be used for carrying the operation unit 3.

As a result of the above construction, when the housing member 30 is positioned such that the open end 35 is oriented toward and spaced apart from a subject M a distance of, for example, 5–30 cm, the subject M can be exposed to the electrostatic field and a flow of the ejected oxygen-containing gas and irradiated with the infrared radiation.

Figure 4:
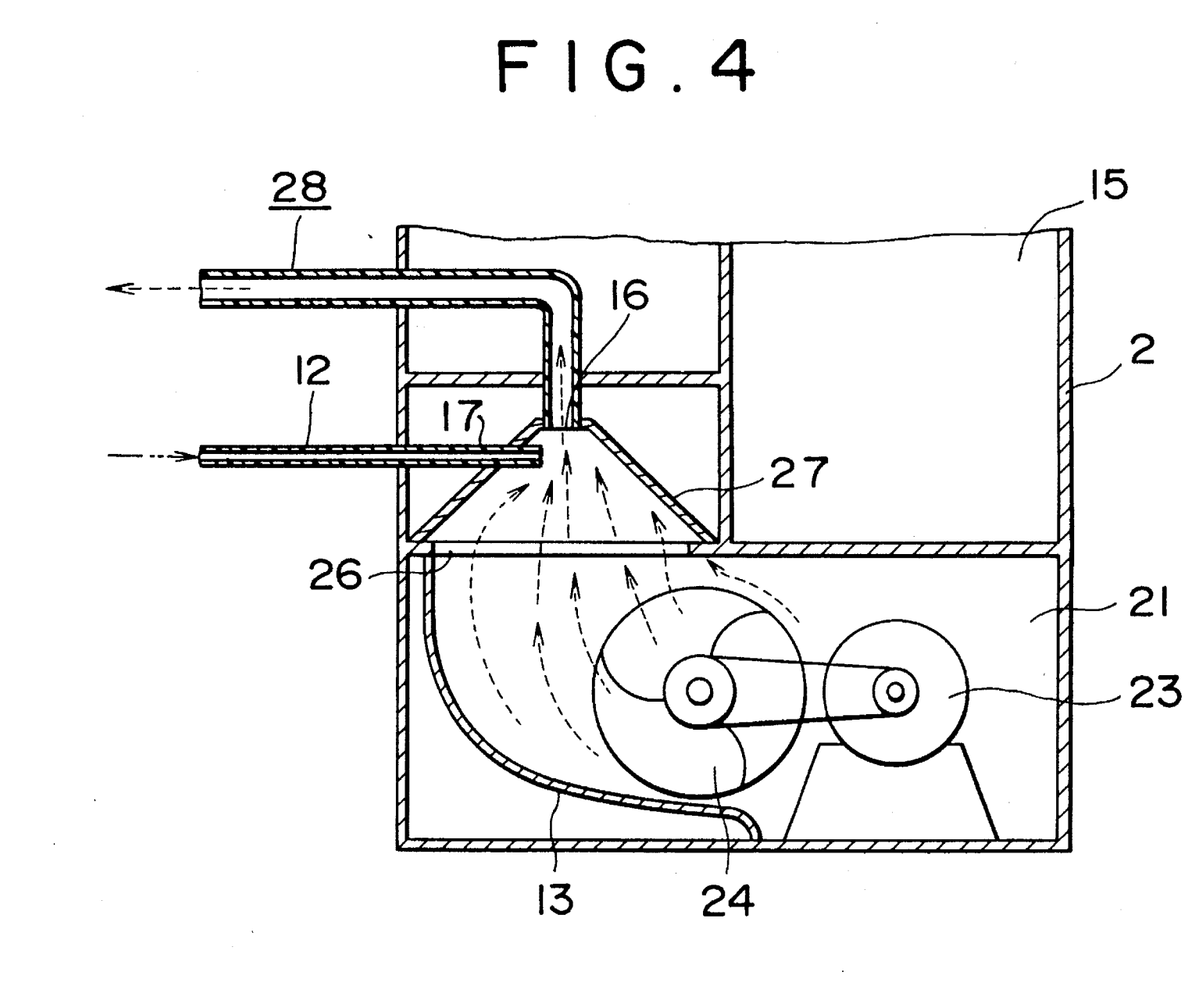
FIG. 4 is a cross-sectional, enlarged, fragmentary, elevational view showing an oxygen-containing gas feeding section of the embodiments of FIG. 1.

Referring to FIGS. 1 and 4, the controlling unit 1 has a frame 2 to which an oxygen-air mixer 27 is fixed. The mixer 27 has a large diameter opening 26 and the previously described oxygen-containing gas feed port 16, having a smaller diameter than that of the opening 26. Fixedly secured to and extending through a side wall of the mixer 27 is a nozzle 17 having an one end positioned adjacent to the gas feed port 16 and the other end connected to a tube, preferably a flexible plastic tube 12. The tube 12 is connected to an oxygen cylinder 11. The large diameter opening 26 is in fluid communication with an air feed chamber 21 defined in the lower part of the controlling unit 1. A fan 24 driven by a motor 23 is disposed in the air feed chamber 21. By rotation of the fan 24, air is introduced through an air intake opening, in the form of a grille 25, into the air feed chamber 21 and is passed through the opening 26 into the mixer 27. The flow of the air is uniformly mixed with the oxygen gas ejected through the nozzle 17 and the resulting oxygen-air mixture is discharged through the port 16 from the mixer 27 to the pipe 28. The mixing is performed so that the concentration of the oxygen in the oxygen-containing gas is generally about 20–50% by volume. The lower limit of about 20% represents a case where air is used by itself as the oxygen-containing gas and no additional oxygen is supplied.

As shown in FIG. 1, the air intake opening 25 is provided with air cleaning means including an air filter 25a, a pair of negative and positive electrodes 25b and 25c, and an ion filter 25d for removing dust, smoke and the microparticles from air. In FIG. 3, the reference numeral 13 designates a guide plate for guiding the air flow to the mixer 27. The reference numeral 15 designates a space for accommodating the operation unit 3 during non-use.

In an upper part of the controlling unit 1, there are provided various electric or electronic devices for controlling the intensity of the infrared radiation of the lamp 32, the voltage impressed to the electrode 33, the rotational speed of the fan 24, the voltage impressed to the electrodes 25b and 25c of the air cleaner, etc. These devices per se are well known in the art and specific explanation thereof is omitted here. 0f course, various instruments such as alarms, timers, indicators, adjusting dials and switches are mounted on a front panel 14.

Figure 5:
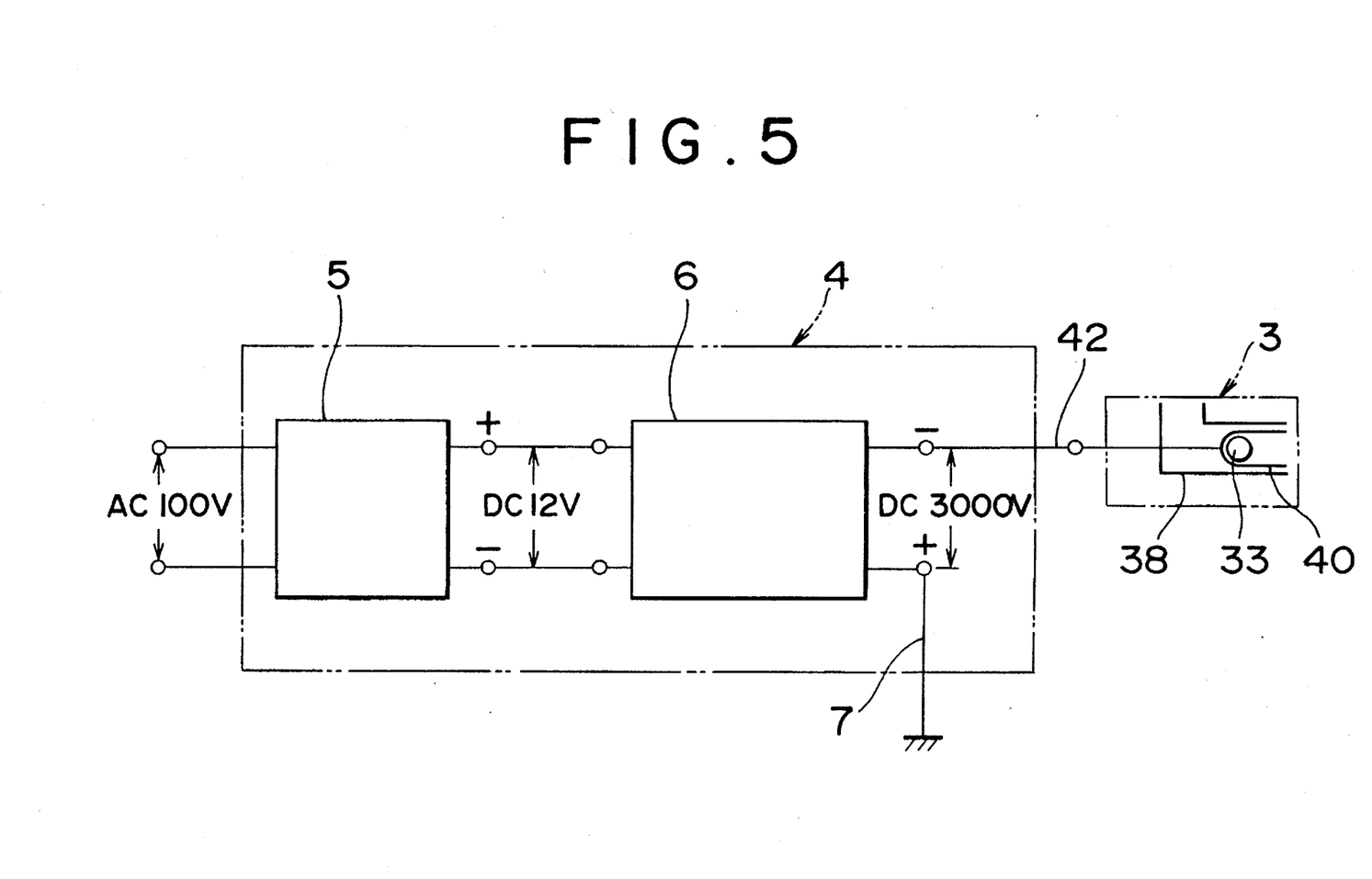
FIGS. 5–8 are diagrams showing different embodiments of high DC voltage generating circuits.

FIG. 5 illustrates one example of a high DC voltage applying circuit system 4. An AC voltage source (e.g. AC 100 volts) is connected to a DC regulated power supply circuit 5 (e.g. DC 12 volts) which in turn is coupled to a high DC voltage power generator 6. A high DC voltage (e.g. 3,000 volts) is impressed to the electrode 33 of the operation unit 3. For the purpose of preventing static problems, the ground-side terminal is connected to a lead wire 7 and is grounded.

Figure 6:
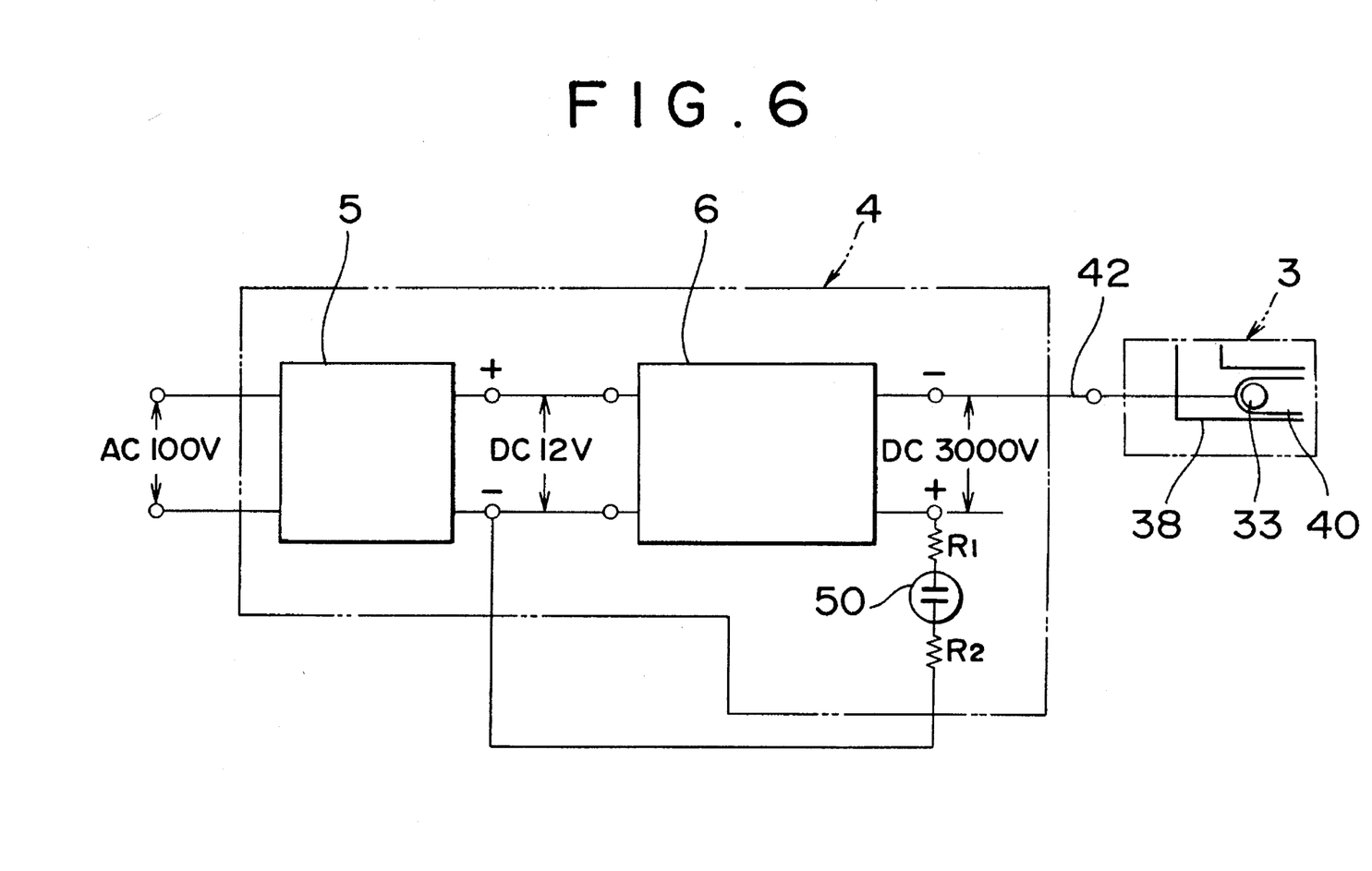
Figure 7:
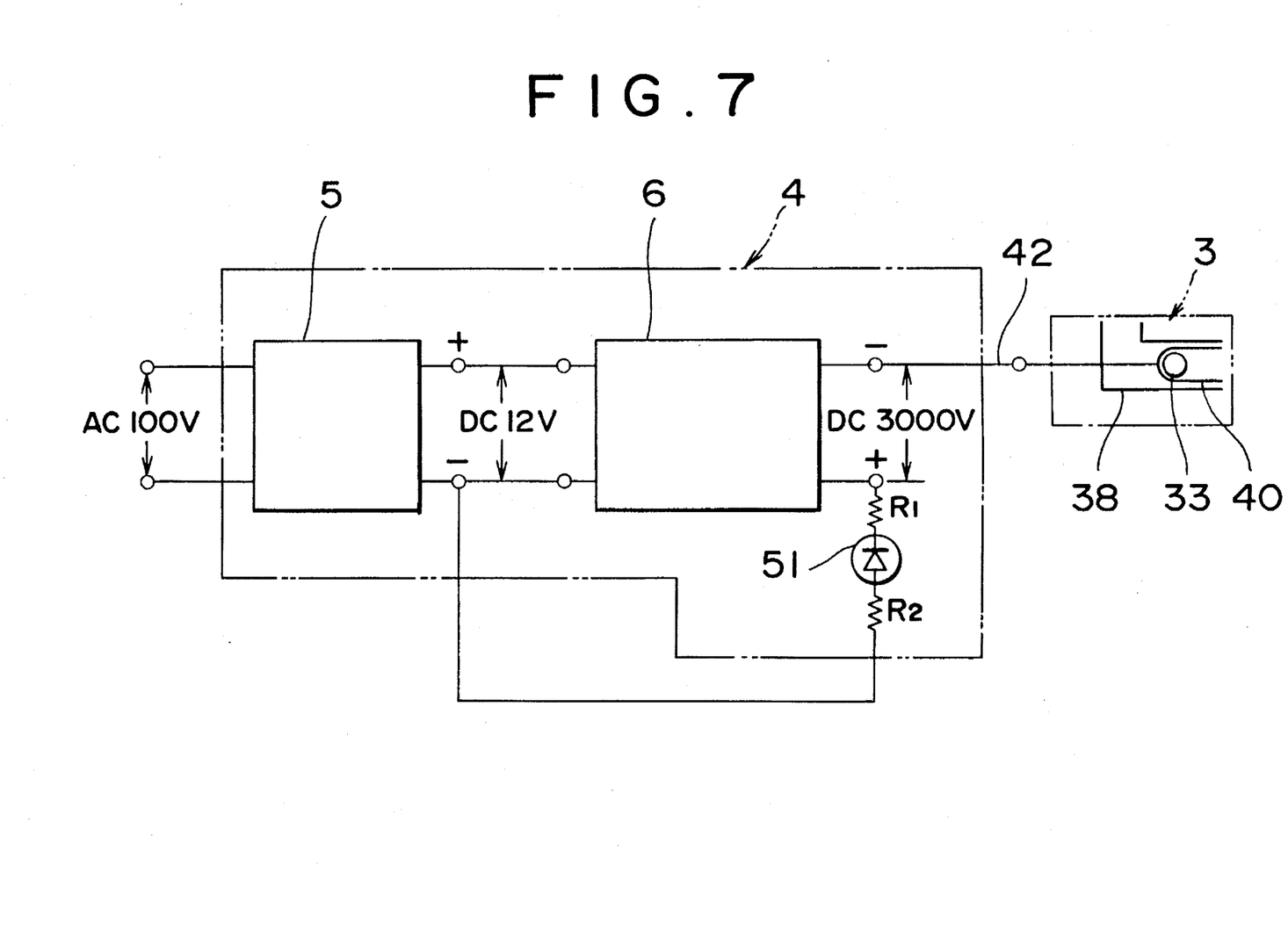
Figure 8:
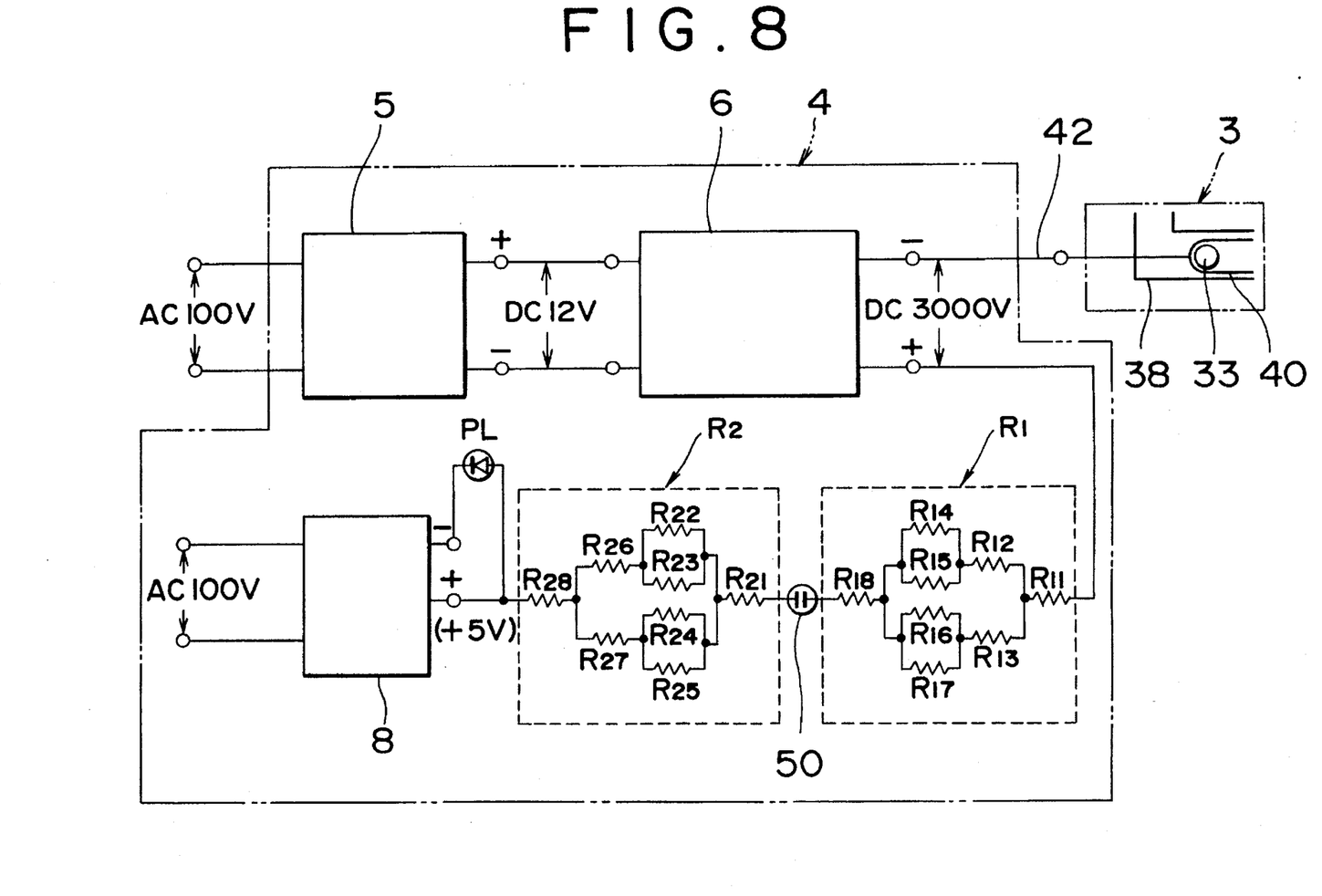

FIGS. 6–8 illustrate further examples of high DC voltage applying circuits 4. In the grounded circuit of FIG. 5, energy loss by leak is unavoidable. Further, because of the presence of the ground wire 7, the location at which the curative apparatus is placed cannot be selected at will. In the circuit shown in FIG. 6, the ground wire 7 is substituted by an electric discharge tube 50 which is adapted to spontaneously operate only when the electric potential between the terminals thereof exceeds a predetermined level of, for example 20 volts, so that the accumulation of an excess static charge in the apparatus is prevented. Such a discharge tube is well known in the art and commercially available. $R_1$ and $R_2$ are resistors.

In the embodiment of FIG. 7, a light emitting diode 51 is substituted for the discharge tube 50 of FIG. 6. The diode 51 is adapted to emit light when the electric potential exceeds a predetermined level of, for example, 3 volts. The light emitting diode 51 may be replaced by a neon tube, if desired.

FIG. 8 illustrates a modification of the circuit of FIG. 6. The modified circuit is provided with a number of resistors $R_{11}$–$R_{18}$ and $R_{21}$–$R_{28}$ for eliminating a static field formed in the space in the controlling unit 1 by recollecting floating charges and introducing same into the circuit. From the viewpoint of operation of the discharge tube 50, the circuits of FIGS. 6 and 8 are equivalent. Designated as 8 is a DC regulated power supply circuit (e.g. DC 5 volts) which is coupled to a pilot lamp PL. The circuit of FIG. 8 is also effective to relax a rush current since the presence of numerous resistors can increase the coil components which can serve to create back electromotive forces acting against the rush current.

The following examples will further illustrate the present invention.

EXAMPLE

A therapeutic device as shown in FIGS. 1–4 and 7 was operated under the following conditions for the treatment of subjects:
Oxygen-Containing Gas Flow:
  (1) Gas velocity: 1.2–5.5 m/sec.
  (2) Oxygen concentration: 20.9–40 % by volume
Infrared Ray Irradiation:
  (1) Wavelength: 0.57–5 μm
Electrostatic Field:
  (1) Electrode: iron ball with a diameter of 25 mm
  (2) Impressed voltage: −3,000 to −7,000 volts
Treatment Conditions:
  (1) Distance between the skin and the electrode: 20–60 cm
  (2) Static Intensity: 20–100 volts/m
  (3) Irradiated Area (diameter): about 20 cm
  (4) Treatment time: 10–15 minutes per one time
  (5) Temperature: 22°–30° C.
  (6) Distance between the skin and the IR lamp: 40–80 cm
The following are individual cases.

A female subject, aged 81, had chronic arthritis in both knees and could neither sit straight nor walk without a walking stick. Treatment with the therapeutic device was daily performed thrice a day. After 3 days treatment, pain became weak. After 6 days from the commencement of the treatment she could stepped down and walked a distance of 100 m. After ten days, she could sit straight.

A female subject, aged 40, had arthritis in both knees. Treatment with the therapeutic device was daily performed not only for the both knees but also for the soles of the feet. Pain lessened after 3 days treatment. After 1 week treatment, she could sit straight. After 3 weeks treatment, she could walk without a weary feeling.

A female subject, aged 29, had lumbago and often suffered severe pain. Application of a poultice and massotherapy were ineffective. Treatment with the therapeutic device was daily performed not only for the loin but also for the soles of the feet for 10 days. The lumbago was alleviated.

A female subject, aged 51, suffered from stiffness in the shoulders for a long time. Treatment with the therapeutic device was daily performed not only for the shoulders but also for the soles of the feet. The stiffness in the shoulders was gradually relaxed after 10 days treatment and disappeared after 20 days treatment.

A male subject, aged 26, had trichophytia in the groin and the crotch. Application of various ointments was not effective. Treatment with the therapeutic device was then daily performed for 3 weeks. After 10 days treatment, crotch itch and rubefaction became weak. After 20 days, hot bath no longer smarted. The trichopytia was effectively treated.

A male subject, aged 42, suffered from mycotic candida dermatitis. Ointments failed to cure the affection. Treatment with the therapeutic device was daily performed three times per day for about one month. After one week treatment, the focus became dark. After two weeks treatment, the rubefaction was almost completely gone. The focus turned brown due to pigmentation, showing effectiveness in the treatment of the candida dermatitis.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

I claim:
1. A therapeutic device comprising:
   an axially extending housing member having an open end;
   an infrared lamp secured within said housing member so that infrared radiation from said lamp passes outwardly through said open end upon energization of said lamp;
   means for feeding an oxygen-containing gas to said housing member;
   a gas pipe disposed within said housing member and having a first end connected to said oxygen-containing gas feeding means and a second end located adjacent to said open end and oriented so that the oxygen-containing gas flows from said second end in the axial direction of said housing member upon actuation of said oxygen-containing gas feeding means;
   a DC voltage source; and
   an electrode disposed adjacent to said second end of said gas pipe and electrically connected to said DC voltage source so that an electrostatic field is formed in the atmosphere adjacent to said open end of said housing member upon actuation of said DC voltage source,
   whereby, when said housing member is positioned such that said open end is oriented toward and spaced apart from a subject, the subject is exposed to the electrostatic field and a flow of the oxygen-containing gas and is irradiated with the infrared radiation.

2. A device according to claim 1, further comprising an oxygen storage container and means for mixing air with oxygen from said storage container to form said oxygen-containing gas having an oxygen content of about 20–50 % by volume.

3. A device according to claim 1, wherein said DC voltage source has such a voltage that said electrostatic field has a field intensity of 20–100 volts per meter.

4. A device according to claim 1, wherein said electrode is a spherical electrode having a diameter of 0.5–5 cm.

5. A device according to claim 4, wherein said electrode is mounted in said gas pipe, said gas pipe having an interior surfaces which defines an annular space in conjunction with said electrode, so that the oxygen-containing gas passes through the annular space.

6. A device according to claim 1, further comprising a control means for controlling a voltage applied to said electrode, a voltage applied to said infrared lamp and a flow rate of said oxygen-containing gas.

7. A device according to claim 6, wherein said said control means is provided with a discharge circuit for preventing accumulation of static charges in said control means.

8. A device according to claim 7, wherein said discharge circuit is a grounded wire, an electric discharge tube or a light emitting diode.

9. A device according to claim 7, wherein said discharge circuit comprises a multiplicity of resistors for collecting static charges within said control means.

\* \* \* \* \*